(12) United States Patent
Casteel, Jr. et al.

(10) Patent No.: US 6,455,728 B1
(45) Date of Patent: Sep. 24, 2002

(54) DIRECT FLUORINATION PROCESS FOR PREPARING HIGH PURITY 2-FLUORO-1,3-DICARBONYL COMPOUNDS USING OXYGEN AS A RADICAL SCAVENGER

(75) Inventors: William Jack Casteel, Jr., Emmaus; Wade H. Bailey, III, Macungie, both of PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 0 days.

(21) Appl. No.: 09/432,723

(22) Filed: Nov. 1, 1999

(51) Int. Cl.[7] ............................................. C07C 69/66
(52) U.S. Cl. ..................... 560/174; 560/178; 568/393
(58) Field of Search .................. 560/174, 178; 568/393

(56) References Cited

U.S. PATENT DOCUMENTS

| 2,614,129 A | * | 10/1952 | McBee et al. ............... 570/148 |
| 4,036,864 A | | 7/1977 | Barton et al. ............. 260/397.3 |
| 4,284,558 A | * | 8/1981 | Barton et al. ................. 540/25 |
| 5,569,778 A | * | 10/1996 | Umemoto et al. .......... 560/121 |

FOREIGN PATENT DOCUMENTS

| EP | 0891962 | | 1/1999 | ........... C07C/45/63 |
| WO | WO 95/14646 | * | 6/1995 | |
| WO | WO 97/35824 | * | 10/1997 | |

OTHER PUBLICATIONS

Chambers et al, Direct Fluorination of 1,3– Dicarbonyl Compounds, Tetrahedron, 52(1), p. 1–8, Jan. 1996.*

Chambers et al, Direct of Fluorination of 1,3– Dicarbonyl compounds, J. Chem. Soc., Chem. Commun., (1), 21–2, Jan. 1995.*

Appelman, "Isolation and Characterization of Acetyl Hypofluorite" J. Am. Chem. Soc. 1985, 1076515–6518.

* cited by examiner

Primary Examiner—Alan L. Rotman
Assistant Examiner—Taylor V Oh
(74) Attorney, Agent, or Firm—Geoffrey L. Chase

(57) ABSTRACT

A process for fluorinating β-dicarbonyls to form the corresponding α-fluorinated-β-dicarbonyl compounds is provided. The process is represented by the following reaction scheme:

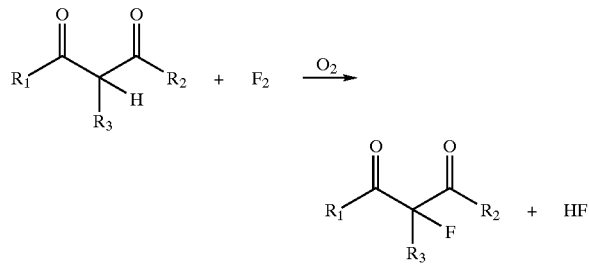

where $R_1$ is H, alkyl or alkoxy, $R_2$ is H, alkyl or perfluoroalkyl, and $R_3$ is H, Cl, Br, I or alkyl. Use of oxygen in the fluorine stream yields a product which is 90–96% pure and contains radical fluorination impurity levels which are 10–20% lower than when oxygen is not used.

17 Claims, No Drawings

DIRECT FLUORINATION PROCESS FOR PREPARING HIGH PURITY 2-FLUORO-1,3-DICARBONYL COMPOUNDS USING OXYGEN AS A RADICAL SCAVENGER

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

This invention relates to processes for fluorinating β-dicarbonyls to form the corresponding α-fluorinated-β-dicarbonyl compounds.

Previously, β-dicarbonyls, such as β-diketones and β-ketoesters, having the formula:

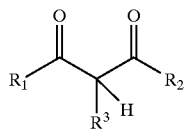

where $R_1$ is H, alkyl or alkoxy, $R_2$ is H, alkyl or perfluoroalkyl, and $R_3$ is H, Cl, Br, I or alkyl, have been fluorinated directly with fluorine in acidic solvents or in polar solvents containing acidic, or weakly basic, polar additives. See, e.g., U.S. Pat. No. 5,569,778 (Umemoto et al.) and WO 95/14646 (Chambers et al.). This technology has proven reasonably selective for those diketones and ketoesters which are stabilized in the enol form under the chosen solvent conditions. Even with substrate loadings of only 5–10 wt. %, however, the desired monofluorinated products still contain 10–15% radical fluorination impurities (the term "radical fluorination impurities" refers to products resulting from fluorination at $R_1$ and/or $R_2$ in Formula I above).

EP 0891962 (Nukui et al.) discloses a process for preparing fluorinated dicarbonyl compounds comprising reacting dicarbonyl compounds and fluorine gas without any solvent and in the presence of at least one acid selected from the group consisting of trifluoromethanesulfonic acid (i.e., triflic acid), methanesulfonic acid, hydrofluoric acid, sulfuric acid, trifluoroacetic acid, boron trifluoride and sulfonated polymers. Nukui et al. discloses in Example 1 that methyl-3-oxopentanoate can be fluorinated in the absence of solvent with triflic acid as an additive, to give only 16% fluorination impurities, including 2,2-difluorinated impurity. The yield was reported to be high only when 2.5 equivalents of fluorine were added.

Ketoesters containing perfluoroalkyl groups are only effectively fluorinated in nonpolar solvents. Under these conditions, 30% radical fluorination is observed. For all of the dicarbonyl substrates, fluorinated impurities are often difficult to separate and many of them are carried forward in subsequent chemical steps.

A further problem in direct fluorinations with formic acid, trifluoroacetic acid and/or triflic acid, has been that fluorine use has been inefficient. Between 1.6 and 4 times the stoichiometric amount of fluorine has been required to obtain high conversions with these acid additives.

Accordingly, it is desired to directly fluorinate β-dicarbonyl compounds by a process that does not suffer from the foregoing deficiencies in the art.

All references cited herein are incorporated herein by reference in their entireties.

BRIEF SUMMARY OF THE INVENTION

The invention comprises a process for providing an α-fluorinated-β-dicarbonyl compound, said process comprising directly fluorinating a β-dicarbonyl compound with fluorine to provide the α-fluorinated-β-dicarbonyl compound, wherein the direct fluorination is conducted in a reactive medium. The reactive medium preferably comprises a radical scavenger, such as oxygen, that inhibits side reactions between fluorine and acid additives.

BRIEF DESCRIPTION OF SEVERAL VIEWS OF THE DRAWINGS

Not applicable.

DETAILED DESCRIPTION OF THE INVENTION

Embodiments of the invention comprise a process which uses dilute oxygen as a radical scavenger for the direct fluorination of β-dicarbonyl compounds, as shown in

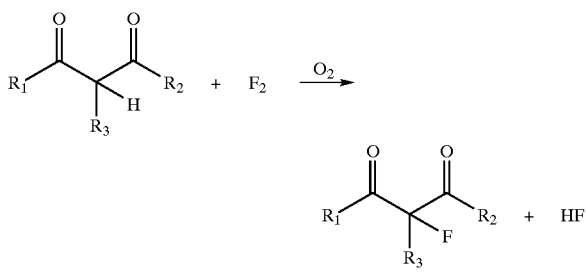

where $R_1$ is H, alkyl or alkoxy, $R_2$ is H, alkyl or perfluoroalkyl, and $R_3$ is H, Cl, Br, I or alkyl. The products of the inventive process (e.g., 2-fluoro-1,3-dicarbonyls) are important precursors to fluorinated heterocycles used in the pharmaceutical industry.

Conventional processes of direct fluorination typically provide fluorinated carbonyl products which are only 75–85% pure and contaminated with radical fluorination byproducts, which are difficult to separate. Use of oxygen in the fluorine stream can lightly lower the overall isolated yield, but after washing with water, yields a product which is 90–96% pure and containing radical fluorination impurity levels which are 5–20% lower than when oxygen is not used. Use of oxygen in the fluorine stream inhibits side reactions between fluorine and acid additives used in direct fluorination (e.g., formic acid, trifluoroacetic acid, and/or triflic acid) so that less fluorine is required to give high substrate conversion.

In embodiments of the inventive process, $F_2/N_2$ mixtures are diluted with air to give dilute $F_2/O_2/N_2$ mixtures, which are sparged into solutions of the substrate in an acidic solvent (for ketoesters where $R_2=R_f$, the solvent is $CFCl_3$). The gas mixture can suitably comprise about 1 to about 50% $F_2$, about 0.1% to about 50% $O_2$ and about 0 to about 99% $N_2$, preferably about 5 to about 25% $F_2$, about 1 to about 25% $O_2$ and about 50 to about 95% $N_2$, more preferably about 10 to about 20% $F_2$, about 10 to about 20% $O_2$ and about 60 to about 80% $N_2$. At high conversions, less than 5% radical fluorination byproducts are observed.

Surprisingly, when oxygen is added during the fluorination, ketoesters (where $R_2=R_f$) can be fluorinated selectively without a solvent. When fluorinated neat in the absence of oxygen, these compounds char, giving only a small amount of the desired product. The process, therefore, offers the advantage of significantly higher product purity obtained at much higher reaction loadings.

The invention will be illustrated in more detail with reference to the following Examples, but it should be understood that the present invention is not deemed to be limited thereto.

EXAMPLES

Example 1

Methyl-3-oxopentanoate was Fluorinated in Neat HF Using $10\%F_2/10\%O_2/80\%N_2$ in Accordance with the Following Procedure.

A 300 mL Parr reactor was charged with 55.1 g (424 mmol) methyl-3-oxopentanoate. The reactor was externally cooled to about −35° C. and 150 mL anhydrous HF were condensed in under static vacuum. This corresponds to a substrate loading of 27 wt. %. About 1.04 equivalents (442 mmol) of $F_2$ were sparged as a $10\%F_2/10\%O_2/80\%N_2$ stream into the reactor at −30° C. at 800 mL/min, allowing the effluent to pass through a soda-lime scrubber. After addition of $F_2$, HF solvent was evacuated through a soda-lime scrubber. The reactor was then opened and 100 mL $H_2O$ were added. The mixture was then neutralized with $NaHCO_3$. The product was extracted with ether.

Analysis of the product by $^1H$ and $^{19}F$ NMR showed 100% conversion. The isolated yield was 81 wt. % of 92% pure methyl-2-fluoro-3-oxopentanoate. Radical fluorination impurities in the isolated product totaled 5%.

Example 2

Methyl-3-oxopentanoate was Fluorinated in Neat HF Using $20\%F_2/20\%O_2/60\%N_2$ in Accordance with the Following Procedure.

A 2 L Parr reactor was charged with 325 g (2.50 mol) methyl-3-oxopentanoate. The reactor was externally cooled to about −50° C. and 1.150 L anhydrous HF were condensed in under static vacuum. This corresponds to a substrate loading of 22 wt. %. About 1.1 equivalents (2.75 mol) of $F_2$ were sparged as a $20\%F_2/20\%O_2/60\%N_2$ stream into the reactor at −30° C. at 800 mL/min, allowing the effluent to pass through a soda-lime scrubber. After addition of $F_2$, HF solvent was evacuated through a soda-lime scrubber. The reactor was then opened and 500 mL $H_2O$ were added. The mixture was then neutralized with $NaHCO_3$. The product was extracted with ether.

Analysis of the product by $^1H$ and $^{19}F$ NMR showed 100% conversion. The isolated yield was 90 wt. % of 94% pure methyl-2-fluoro-3-oxopentanoate. Radical fluorination impurities in the isolated product totaled 4%.

Example 3

Methyl-3-oxopentanoate was Fluorinated in Neat HF Using $10\%F_2/40\%O_2/50\%N_2$ in Accordance with the Following Procedure.

A 300 mL Parr reactor was charged with 54.3 g (418 mmol) methyl-3-oxopentanoate. The reactor was externally cooled to about −35° C. and 155 mL anhydrous HF were condensed in under static vacuum. This corresponds to a substrate loading of 26 wt. %. About 1.07 equivalents (449 mmol) of $F_2$ were sparged as a $10\%F_2/40\%O_2/50\%N_2$ stream into the reactor at −30° C. at 800 mL/min, allowing the effluent to pass through a soda-lime scrubber. After addition of $F_2$, HF solvent was evacuated through a soda-lime scrubber. The reactor was then opened and 100 mL $H_2O$ were added. The mixture was then neutralized with $NaHCO_3$. The product was extracted with ether.

Analysis of the product by $^1H$ and $^{19}F$ NMR showed 100% conversion. The isolated yield was 78 wt. % of 93% pure methyl-2-fluoro-3-oxopentanoate. Radical fluorination impurities in the isolated product totaled 5%.

Example 4

Methyl-3-oxopentanoate was Fluorinated in Neat HF Using $10\%F_2/90\%N_2$ in Accordance with the Following Comparative Example.

A 300 mL Parr reactor was charged with 59.5 g (458 mmol) methyl-3-oxopentanoate. The reactor was externally cooled to about −35° C. and 155 mL anhydrous HF were condensed in under static vacuum. This corresponds to a substrate loading of 28 wt. %. About 1.06 equivalents (484 mmol) of $F_2$ were sparged as a $10\%F_2/90\%N_2$ stream into the reactor at −30° C. at 800 mL/min, allowing the effluent to pass through a soda-lime scrubber. After addition of $F_2$, HF solvent was evacuated through a soda-lime scrubber. The reactor was then opened and 100 mL $H_2O$ were added. The mixture was then neutralized with $NaHCO_3$. The product was extracted with ether.

Analysis of the product by $^1H$ and $^{19}F$ NMR showed 99% conversion. The isolated yield was 91 wt. % of 81% pure methyl-2-fluoro-3-oxopentanoate. Radical fluorination impurities in the isolated product totaled 15%.

Example 5

Methyl-3-oxopentanoate was Fluorinated in Neat HF Using $10\%F_2/90\%N_2$ in Accordance with the Following Comparative Example.

A 60 mL Parr reactor was charged with 5.17 g (39.8 mmol) methyl-3-oxopentanoate. The reactor was externally cooled to about −35° C. and 20 mL anhydrous HF were condensed in under static vacuum. This corresponds to a substrate loading of 20 wt. %. About 1.11 equivalents (484 mmol) of $F_2$ were sparged as a $10\%F_2/90\%N_2$ stream into the reactor at −30° C. at 200 mL/min, allowing the effluent to pass through a soda-lime scrubber. After addition of $F_2$, HF solvent was evacuated through a soda-lime scrubber. The reactor was then opened and 100 mL $H_2O$ were added. The mixture was then neutralized with $NaHCO_3$. The product was extracted with ether.

Analysis of the product by $^1H$ and $^{19}F$ NMR showed 96% conversion. The isolated yield was 87 wt. % of 86% pure methyl-2-fluoro-3-oxopentanoate. Radical fluorination impurities in the isolated product totaled 9.4%.

Example 6

Methyl-3-oxopentanoate was Fluorinated in Neat HF Using $10\%F_2/1\%O_2/89\%N_2$ in Accordance with the Following Procedure.

A 60 mL FEP reactor was charged with 4.64 g (35.6 mmol) methyl-3-oxopentanoate. The reactor was externally cooled to about −50° C. and 20 mL anhydrous HF were condensed in under static vacuum. This corresponds to a substrate loading of 19 wt. %. About 1.13 equivalents (40.2 mmol) of $F_2$ were sparged as a $10\%F_2/1\%O_2/89\%N_2$ stream into the reactor at −30° C. at 200 mL/min, allowing the effluent to pass through a soda-lime scrubber. After addition of $F_2$, HF solvent was evacuated through a soda-lime scrubber. The reactor was then opened and 30 mL $H_2O$ were added. The mixture was then neutralized with $NaHCO_3$. The product was extracted with ether.

Analysis of the product by $^1H$ and $^{19}F$ NMR showed 100% conversion. The isolated yield was 80 wt. % of 95% pure methyl-2-fluoro-3-oxopentanoate. Radical fluorination impurities in the isolated product totaled 3%.

Example 7

Methyl-3-oxopentanoate was Fluorinated in Neat HF Using 10%$F_2$/0.1%$O_2$/89.9%$N_2$ in Accordance with the Following Procedure.

A 60 mL FEP reactor was charged with 4.08 g (31.4 mmol) methyl-3-oxopentanoate. The reactor was externally cooled to about −50° C. and 20 mL anhydrous HF were condensed in under static vacuum. This corresponds to a substrate loading of 17 wt. %. About 1.13 equivalents (40.2 mmol) of $F_2$ were sparged as a 10%$F_2$/0.1%$O_2$/89.9%$N_2$ stream into the reactor at −30° C. at 200 mL/min, allowing the effluent to pass through a soda-lime scrubber. After addition of $F_2$, HF solvent was evacuated through a soda-lime scrubber. The reactor was then opened and 30 mL $H_2O$ were added. The mixture was then neutralized with $NaHCO_3$. The product was extracted with ether.

Analysis of the product by $^1H$ and $^{19}F$ NMR showed 100% conversion. The isolated yield was 80 wt. % of 95% pure methyl-2-fluoro-3-oxopentanoate. Radical fluorination impurities in the isolated product totaled 3%.

Example 8

Methyl-3-oxopentanoate was Fluorinated in Neat HF Using 10%$F_2$/10%$O_2$/80%$N_2$ in Accordance with the Following Procedure.

A 100 mL FEP reactor was charged with 25.6 g (197 mmol) methyl-3-oxopentanoate. The reactor was externally cooled to about −50° C. and 42 mL anhydrous HF were condensed in under static vacuum. This corresponds to a substrate loading of 38 wt. %. About 1.10 equivalents (217 mmol) of $F_2$ were sparged as a 10%$F_2$/10%$O_2$/80%$N_2$ stream into the reactor at −30° C. at 300 mL/min, allowing the effluent to pass through a soda-lime scrubber. After addition of $F_2$, HF solvent was evacuated through a soda-lime scrubber. The reactor was then opened and 30 mL $H_2O$ were added. The mixture was then neutralized with $NaHCO_3$. The product was extracted with ether.

Analysis of the product by $^1H$ and $^{19}F$ NMR showed 100% conversion. The isolated yield was 80 wt. % of 85% pure methyl-2-fluoro-3-oxopentanoate. Radical fluorination impurities in the isolated product totaled 11%.

Example 9

Methyl-3-oxopentanoate was Fluorinated in Neat HF Using 10%$F_2$/10%$O_2$/80%$N_2$ in Accordance with the Following Procedure.

A 100 mL FEP reactor was charged with 15.3 g (118 mmol) methyl-3-oxopentanoate. The reactor was externally cooled to about −50° C. and 23 mL anhydrous HF were condensed in under static vacuum. This corresponds to a substrate loading of 40 wt. %. About 1.02 equivalents (120 mmol) of $F_2$ were sparged as a 10%$F_2$/10%$O_2$/80%$N_2$ stream into the reactor at −45° C. at 300 mL/min, allowing the effluent to pass through a soda-lime scrubber. After addition of $F_2$, HF solvent was evacuated through a soda-lime scrubber. The reactor was then opened and 30 mL $H_2O$ were added. The mixture was then neutralized with $NaHCO_3$. The product was extracted with ether.

Analysis of the product by $^1H$ and $^{19}F$ NMR showed 96% conversion. The isolated yield was 87 wt. % of 90% pure methyl-2-fluoro-3-oxopentanoate. Radical fluorination impurities in the isolated product totaled 6%.

Example 10

Methyl-3-oxopentanoate was Fluorinated in Trifluoroacetic Acid (TFA) Using 10%$F_2$/10%$O_2$/80%$N_2$ in Accordance with the Following Procedure.

A 100 mL FEP reactor was charged with 5.2 g (40 mmol) methyl-3-oxopentanoate and 29 g TFA. This corresponds to a substrate loading of 18 wt. %. About 1.2 equivalents (48 mmol) of $F_2$ were sparged as a 10%$F_2$/10%$O_2$/80%$N_2$ stream into the reactor at −15° C. at 300 mL/min, allowing the effluent to pass through a soda-lime scrubber. After addition of $F_2$, TFA solvent was evacuated through a soda-lime scrubber. The reactor was then opened and 30 mL $H_2O$ were added. The mixture was then neutralized with $NaHCO_3$. The product was extracted with ether.

Analysis of the product by $^1H$ and $^{19}F$ NMR showed 95% conversion. The isolated product was 84% pure methyl-2-fluoro-3-oxopentanoate. Radical fluorination impurities in the isolated product totaled 7%.

Example 11

Methyl-3-oxopentanoate was Fluorinated in TFA Using 10%$F_2$/90%$N_2$ in Accordance with the Following Comparative Example.

A 100 mL FEP reactor was charged with 5.2 g (40 mmol) methyl-3-oxopentanoate and 26 g TFA. This corresponds to a substrate loading of 20 wt. %. About 1.5 equivalents (60 mmol) of $F_2$ were sparged as a 10%$F_2$/90%$N_2$ stream into the reactor at −20° C. at 300 mL/min, allowing the effluent to pass through a soda-lime scrubber. After addition of $F_2$, TFA solvent was evacuated through a soda-lime scrubber. The reactor was then opened and 30 mL $H_2O$ were added. The mixture was then neutralized with $NaHCO_3$. The product was extracted with ether.

Analysis of the product by $^1H$ and $^{19}F$ NMR showed 85% conversion. The isolated product was 60% pure methyl-2-fluoro-3-oxopentanoate. Radical fluorination impurities in the isolated product totaled 12%.

Example 12

Methyl-3-oxopentanoate was Fluorinated in Formic Acid Using 10%$F_2$/10%$O_2$/80%$N_2$ in Accordance with the Following Procedure.

A 100 mL FEP reactor was charged with 7.2 g (55 mmol) methyl-3-oxopentanoate and 26 g formic acid. This corresponds to a substrate loading of 22 wt. %. About 1.06 equivalents (59 mmol) of $F_2$ were sparged as a 10%$F_2$/10%$O_2$/80%$N_2$ stream into the reactor at 5° C. at 300 mL/min, allowing the effluent to pass through a soda-lime scrubber. After addition of $F_2$, the reactor was opened and 30 mL $H_2O$ were added. The mixture was then neutralized with $NaHCO_3$. The product was extracted with ether.

Analysis of the product by $^1H$ and $^{19}F$ NMR showed 98% conversion. The isolated product was 75% of 88% pure methyl-2-fluoro-3-oxopentanoate. Radical fluorination impurities in the isolated product totaled 7%.

Example 13

Methyl-3-oxopentanoate was Fluorinated in Formic Acid Using 10%$F_2$/90%$N_2$ in Accordance with the Following Comparative Example.

A 100 mL FEP reactor was charged with 7.0 g (54 mmol) methyl-3-oxopentanoate and 25 g formic acid. This corresponds to a substrate loading of 22 wt. %. About 1.04 equivalents (56 mmol) of $F_2$ were sparged as a 10%$F_2$/10%$O_2$/80%$N_2$ stream into the reactor at 5° C. at 300 mL/min, allowing the effluent to pass through a soda-lime scrubber. After addition of $F_2$, the reactor was opened and 30 mL $H_2O$ were added. The mixture was then neutralized with $NaHCO_3$. The product was extracted with ether.

Analysis of the product by $^1H$ and $^{19}F$ NMR showed 69% conversion. The isolated product was 77% of 55% pure methyl-2-fluoro-3-oxopentanoate. Radical fluorination impurities in the isolated product totaled 8%.

Example 14
Methyl-3-oxopentanoate was Fluorinated in Triflic Acid Using 10%$F_2$/10%$O_2$/80%$N_2$ in Accordance with the Following Procedure.

A 60 mL FEP reactor was charged with 8.27 g (63.6 mmol) methyl-3-oxopentanoate and 1.08 g triflic acid. This corresponds to a substrate loading of 88 wt. %. About 1.21 equivalents (77 mmol) of $F_2$ were sparged as a 10%$F_2$/10%$O_2$/80%$N_2$ stream into the reactor at 0° C. at 100 mL/min, allowing the effluent to pass through a soda-lime scrubber. After addition of $F_2$, triflic acid solvent was evacuated through a soda-lime scrubber. The reactor was then opened and 30 mL $H_2O$ were added. The mixture was then neutralized with $NaHCO_3$. The product was extracted with ether.

Analysis of the product by $^1H$ and $^{19}F$ NMR showed 86% conversion. The isolated product was 72% pure methyl-2-fluoro-3-oxopentanoate. Radical fluorination impurities in the isolated product totaled 13%.

Example 15
Ethyl Acetoacetate was Fluorinated in HF Using 10%$F_2$/10%$O_2$/80%$N_2$ in Accordance with the Following Procedure.

A 100 mL FEP reactor was charged with ethyl acetoacetate (80 mmol). The reactor was externally cooled to about –50° C. and 40 mL anhydrous HF were condensed in under static vacuum. This corresponds to a substrate loading of 20 wt. %. About 1.1 equivalents of $F_2$ were sparged as a 10%$F_2$/10%$O_2$/80%$N_2$ stream into the reactor at –30° C. at 300 mL/min, allowing the effluent to pass through a soda-lime scrubber. After addition of $F_2$, HF solvent was evacuated through a soda-lime scrubber. The reactor was then opened and 30 mL $H_2O$ were added. The mixture was then neutralized with $NaHCO_3$. The product was extracted with ether.

Analysis of the product by $^1H$ and $^{19}F$ NMR showed 96% conversion. The isolated product was 91% pure ethyl-2-fluoroacetoacetate. Radical fluorination impurities in the isolated product totaled 4%.

Example 16
Ethyl acetoacetate was Fluorinated in HF Using 10%$F_2$/90%$N_2$ in accordance with the Following Comparative Example.

A 60 mL FEP reactor was charged with ethyl acetoacetate (40 mmol). The reactor was externally cooled to about –50° C. and 20 mL anhydrous HF were condensed in under static vacuum. This corresponds to a substrate loading of 20 wt. %. About 1.1 equivalents of $F_2$ were sparged as a 10%$F_2$/90%$N_2$ stream into the reactor at –30° C. at 300 mL/min, allowing the effluent to pass through a soda-lime scrubber. After addition of $F_2$, HF solvent was evacuated through a soda-lime scrubber. The reactor was then opened and 30 mL $H_2O$ were added. The mixture was then neutralized with $NaHCO_3$. The product was extracted with ether.

Analysis of the product by $^1H$ and $^{19}F$ NMR showed 90% conversion. The isolated product was 73% pure ethyl-2-fluoroacetoacetate. Radical fluorination impurities in the isolated product totaled 16%.

Example 17
2,4-pentanedione was Fluorinated in HF Using 10%$F_2$/10%$O_2$/80%$N_2$ in Accordance with the Following Procedure.

A 60 mL FEP reactor was charged with 2,4-pentanedione (25 mmol). The reactor was externally cooled to about –50° C. and 15 mL anhydrous HF were condensed in under static vacuum. This corresponds to a substrate loading of 20 wt. %. About 1.1 equivalents of $F_2$ were sparged as a 10%$F_2$/10%$O_2$/80%$N_2$ stream into the reactor at –65° C. at 300 mL/min, allowing the effluent to pass through a soda-lime scrubber. After addition of $F_2$, HF solvent was evacuated through a soda-lime scrubber. The reactor was then opened and 30 mL $H_2O$ were added. The mixture was then neutralized with $NaHCO_3$. The product was extracted with ether.

Analysis of the product by $^1H$ and $^{19}F$ NMR showed 98% conversion. The isolated product was 95% pure 3-fluoro-2,4-pentanedione. Radical fluorination impurities in the isolated product totaled 3%.

Example 18
2,4-pentanedione was Fluorinated in HF Using 10%$F_2$/90%$N_2$ in accordance with the Following Comparative Example.

A 60 mL FEP reactor was charged with 2,4-pentanedione (25 mmol). The reactor was externally cooled to about –50° C. and 15 mL anhydrous HF were condensed in under static vacuum. This corresponds to a substrate loading of 20 wt. %. About 1.1 equivalents of $F_2$ were sparged as a 10%$F_2$/90%$N_2$ stream into the reactor at –65° C. at 300 mL/min, allowing the effluent to pass through a soda-lime scrubber. After addition of $F_2$, HF solvent was evacuated through a soda-lime scrubber. The reactor was then opened and 30 mL $H_2O$ were added. The mixture was then neutralized with $NaHCO_3$. The product was extracted with ether.

Analysis of the product by $^1H$ and $^{19}F$ NMR showed 96% conversion. The isolated product was 93% pure 3-fluoro-2,4-pentanedione. Radical fluorination impurities in the isolated product totaled 3%.

Example 19
Ethyl-4,4,4,-trifluoroacetoacetate was Fluorinated in $CFCl_3$ Using 10%$F_2$/10%$O_2$/80%$N_2$ in Accordance with the Following Procedure.

A 60 mL FEP reactor was charged with ethyl-4,4,4,-trifluoroacetoacetate (20 mmol) and 15 g $CFCl_3$. This corresponds to a substrate loading of 15 wt. %. About 1.0 equivalent of $F_2$ was sparged as a 10%$F_2$/10%$O_2$/80%$N_2$ stream into the reactor at –25° C. at 300 mL/min, allowing the effluent to pass through a soda-lime scrubber. After addition of $F_2$, $CFCl_3$ solvent was evacuated through a soda-lime scrubber. The reactor was then opened and 30 mL $H_2O$ were added. The mixture was then neutralized with $NaHCO_3$. The product was extracted with ether.

Analysis of the product by $^1H$ and $^{19}F$ NMR showed 85% conversion. The isolated product was 80% pure ethyl-2,4,4,4,-tetrafluoroacetoacetate. Radical fluorination impurities in the isolated product totaled 3%.

Example 20
Ethyl-4,4,4,-trifluoroacetoacetate was Fluorinated in $CFCl_3$ Using 10%$F_2$/90%$N_2$ in Accordance with the Following Comparative Example.

A 60 mL FEP reactor was charged with ethyl-4,4,4,-trifluoroacetoacetate (20 mmol) and 15 g $CFCl_3$. This corresponds to a substrate loading of 15 wt. %. About 1.0 equivalent of $F_2$ was sparged as a 10%$F_2$/90%$N_2$ stream into the reactor at –25° C. at 300 mL/min, allowing the effluent to pass through a soda-lime scrubber. After addition of $F_2$, $CFCl_3$ solvent was evacuated through a soda-lime scrubber. The reactor was then opened and 30 mL $H_2O$ were added. The mixture was then neutralized with $NaHCO_3$. The product was extracted with ether.

Analysis of the product by $^1$H and $^{19}$F NMR showed 80% conversion. The isolated product was 45% pure ethyl-2,4,4,4,-tetrafluoroacetoacetate. Radical fluorination impurities in the isolated product totaled 30%.

Example 21

Ethyl-4,4,4,-trifluoroacetoacetate was Fluorinated Using 2%$F_2$/18%$O_2$/80%$N_2$ in Accordance with the Following Procedure.

A 60 mL FEP reactor was charged with ethyl-4,4,4,-trifluoroacetoacetate (20 mmol). About 1.0 equivalent of $F_2$ was sparged as a 2%$F_2$/18%$O_2$/80%$N_2$ stream into the reactor at −30° C. at 300 mL/min, allowing the effluent to pass through a soda-lime scrubber. The reactor was then opened and 30 mL $H_2O$ were added. The mixture was then neutralized with $NaHCO_3$. The product was extracted with ether.

Analysis of the product by $^1$H and $^{19}$F NMR showed 75% conversion. The isolated product was 65% pure ethyl-2,4,4,4,-tetrafluoroacetoacetate. Radical fluorination impurities in the isolated product totaled 5%.

Example 22

Ethyl-4,4,4,-trifluoroacetoacetate was Fluorinated Using 2%$F_2$/98%$N_2$ in Accordance with the Following Comparative Example.

A 60 mL FEP reactor was charged with ethyl-4,4,4,-trifluoroacetoacetate (20 mmol). About 1.0 equivalent of $F_2$ was sparged as a 2%$F_2$/98%$N_2$ stream into the reactor at −40° C. at 300 mL/min, allowing the effluent to pass through a soda-lime scrubber. The reactor was then opened and 30 mL $H_2O$ were added. The mixture was then neutralized with $NaHCO_3$. The product was extracted with ether.

Analysis of the product by $^1$H and $^{19}$F NMR showed 80% conversion. The isolated product was less than 5% pure ethyl-2,4,4,4,-tetrafluoroacetoacetate. Radical fluorination impurities in the isolated product totaled 80%.

The results from the foregoing examples are summarized in the following table (along with an example from Nukui et al.):

| example | substrate | added oxygen | solvent | F2 (equiv) | loading (wt. %) | T (C) | conversion | isolated purity[a] | radical fluorination |
|---|---|---|---|---|---|---|---|---|---|
| 1 | methyl-3-oxopentanoate | yes (10%) | HF | 1.04 | 27 | −30 | 100% | 92% | 5% |
| 2 | methyl-3-oxopentanoate | yes (20%) | HF | 1.1 | 22 | −30 | 100% | 94% | 4% |
| 3 | methyl-3-oxopentanoate | yes (40%) | HF | 1.07 | 26 | −30 | 100% | 93% | 5% |
| 4 | methyl-3-oxopentanoate | no | HF | 1.06 | 28 | −30 | 99% | 81% | 15% |
| 5 | methyl-3-oxopentanoate | no | HF | 1.11 | 20 | −30 | 96% | 86% | 9.4% |
| 6 | methyl-3-oxopentanoate | yes (1%) | HF | 1.13 | 19 | −30 | 100% | 95% | 3% |
| 7 | methyl-3-oxopentanoate | yes (0.1%) | HF | 1.13 | 17 | −30 | 100% | 95% | 3% |
| 8 | methyl-3-oxopentanoate | yes (10%) | HF | 1.1 | 38 | −30 | 100% | 85% | 11% |
| 9 | methyl-3-oxopentanoate | yes (10%) | HF | 1.02 | 40 | −45 | 96% | 90% | 6% |
| 10 | methyl-3-oxopentanoate | yes (10%) | TFA | 1.2 | 18 | −15 | 95% | 84% | 7% |
| 11 | methyl-3-oxopentanoate | no | TFA | 1.5 | 20 | −20 | 85% | 60% | 12% |
| 12 | methyl-3-oxopentanoate | yes (10%) | HCOOH | 1.06 | 22 | 5 | 98% | 88% | 7% |
| 13 | methyl-3-oxopentanoate | no | HCOOH | 1.04 | 22 | 5 | 69% | 55% | 8% |
| 14 | methyl-3-oxopentanoate | yes (10%) | triflic acid | 1.21 | 88 | 0 | 86% | 70% | 13% |
| n/a[b] | methyl-3-oxopentanoate | no | triflic acid | 2.5 | 87 | 0 | n/a | 82.5% | 8.5% |
| 15 | ethyl acetoacetate | yes (10%) | HF | 1.1 | 20 | −30 | 96% | 91% | 4% |
| 16 | ethyl acetoacetate | no | HF | 1.1 | 20 | −30 | 90% | 73% | 16% |
| 17 | 2,4-pentanedione | yes (10%) | HF | 1.1 | 20 | −65 | 98% | 95% | 3% |
| 18 | 2,4-pentanedione | no | HF | 1.1 | 20 | −65 | 96% | 93% | 3% |
| 19 | ethyl-4,4,4-trifluoroacetoacetate | yes (10%) | $CFCl_3$ | 1 | 15 | −25 | 85% | 80% | 3% |
| 20 | ethyl-4,4,4-trifluoroacetoacetate | no | $CFCl_3$ | 1 | 15 | −25 | 80% | 45% | 30% |
| 21 | ethyl-4,4,4-trifluoroacetoacetate | yes (18%) | neat | 1 | 100 | −30 | 75% | 65% | 5% |
| 22 | ethyl-4,4,4-trifluoroacetoacetate | no | neat | 1 | 100 | −40 | 80% | <5% | 80% |

[a]Unfluorinated starting material, α,α-difluorinated material, as well as radical fluorination products, are included as impurities in calculation of the isolated purity.
[b]EP 0891962 (Nukui et al.) at Example 1.

While the invention has been described in detail and with reference to specific examples thereof, it will be apparent to one skilled in the art that various changes and modifications can be made therein without departing from the spirit and scope thereof.

What is claimed is:

1. A process for providing an α-fluorinated-β-dicarbonyl compound, said process comprising directly fluorinating a β-dicarbonyl compound with fluorine to provide said α-fluorinated-β-dicarbonyl compound, wherein said direct fluorination is conducted in a medium comprising oxygen and wherein said process further provides fluorination impurities in an amount less than 15 wt. % based on a combined post-reaction weight of said α-fluorinated-β-dicarbonyl compound, an unreacted portion of said β-dicarbonyl compound, radical fluorination impurities and α,α-difluorination impurities.

2. The process of claim 1, wherein said oxygen is provided at a concentration of at least 0.1 wt. %.

3. The process of claim 1, wherein less than 2.5 equivalents of said fluorine are added per equivalent of said β-dicarbonyl compound.

4. The process of claim 1, wherein less than 1.6 equivalents of said fluorine are added per equivalent of said β-dicarbonyl compound.

5. The process of claim 1, wherein less than 1.3 equivalents of said fluorine are added per equivalent of said β-dicarbonyl compound.

6. The process of claim 1, wherein said amount of said fluorination impurities is less than 10 wt. %.

7. The process of claim 1, wherein said amount of said fluorination impurities includes less than 5 wt. % radical fluorination impurities based on said combined post-reaction weight.

8. The process of claim 1, wherein said α-fluorinated-β-dicarbonyl compound accounts for at least 90 wt. % of said combined post-reaction weight.

9. The process of claim 1, wherein said α-fluorinated-β-dicarbonyl compound accounts for about 90 wt. % to about 96 wt. % of said combined post-reaction weight.

10. The process of claim 1, wherein said process further comprises contacting said α-fluorinated-β-dicarbonyl compound with a gas mixture comprising about 1 to about 50 wt. % $F_2$, about 0.1 to about 50 wt. % $O_2$ and about 0 to about 99 wt. % $N_2$.

11. The process of claim 1, wherein said process further comprises contacting said α-fluorinated-β-dicarbonyl compound with a gas mixture comprising about 5 to about 25 wt. % $F_2$, about 1 to about 25 wt. % $O_2$ and about 50 to about 95 wt. % $N_2$.

12. The process of claim 1, wherein said process further comprises contacting said α-fluorinated-β-dicarbonyl compound with a gas mixture comprising about 10 to about 20 wt. % $F_2$, about 10 to about 20 wt. % $O_2$ and about 60 to about 80 wt. % $N_2$.

13. The process of claim 1, wherein said β-dicarbonyl compound is a ketoester containing an $R_f$ group, and said process is conducted without a solvent or acid additive.

14. The process of claim 1, wherein said β-dicarbonyl compound is a 1,3-diketone and said α-fluorinated-β-dicarbonyl compound is a 2-fluoro-1,3-diketone.

15. The process of claim 1, wherein said β-dicarbonyl compound is not methyl-3-oxopentanoate.

16. A fluorination process represented by the following reaction scheme:

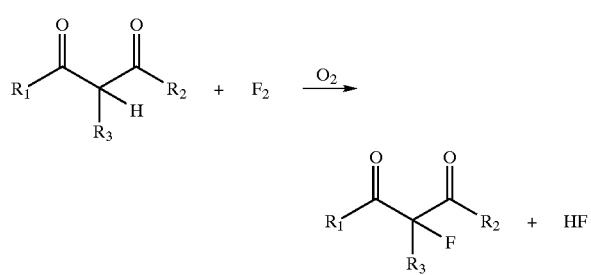

17. The process of claim 1, wherein said process provides no more than 5 wt. % of said α,α-difluorination impurities, based on said combined post-reaction weight.

* * * * *

UNITED STATES PATENT AND TRADEMARK OFFICE
CERTIFICATE OF CORRECTION

PATENT NO. : 6,455,728 B1
DATED : September 24, 2002
INVENTOR(S) : William Jack Casteel, Jr. et al.

It is certified that error appears in the above-identified patent and that said Letters Patent is hereby corrected as shown below:

Column 12,
Line 36, add the following:
-- where $R_1$ is H, alkyl or alkoxy, $R_2$ is H, alkyl or perfluoroalkyl, and $R_3$ is H, Cl, Br, or alkyl, wherein said process further provides fluorination impurities in an amount less than 15 wt.% based on a combined post-reaction weight of α-monofluorinated-β-dicarbonyl product, unreacted β-dicarbonyl reagent, radical fluorination impurities and α, α-difluorination impurities. --

Signed and Sealed this

Seventeenth Day of June, 2003

JAMES E. ROGAN
*Director of the United States Patent and Trademark Office*